United States Patent [19]
Cole

[11] Patent Number: 5,888,524
[45] Date of Patent: *Mar. 30, 1999

[54] ANTIMICROBIAL COMPOSITIONS AND WET WIPES INCLUDING THE SAME

[75] Inventor: Douglas Bryan Cole, Appleton, Wis.

[73] Assignee: Kimberly-Clark Worldwide, Inc., Neenah, Wis.

[*] Notice: The term of this patent shall not extend beyond the expiration date of Pat. No. 5,700,842.

[21] Appl. No.: 902,363

[22] Filed: Jul. 29, 1997

Related U.S. Application Data

[63] Continuation of Ser. No. 548,347, Nov. 1, 1995, abandoned.

[51] Int. Cl.[6] ............................. A61K 9/10; A61K 9/70
[52] U.S. Cl. ..................... 424/402; 424/414; 424/443; 424/404; 424/405; 514/938; 514/943
[58] Field of Search ........................... 424/402, 414, 424/443, 404, 405, 450; 514/721, 943, 938, 975

[56] References Cited

U.S. PATENT DOCUMENTS

| | | | |
|---|---|---|---|
| 3,652,764 | 3/1972 | Lamberti et al. | 424/235 |
| 3,700,601 | 10/1972 | Bloching | 252/105 |
| 3,947,576 | 3/1976 | Kuczkowski et al. | 424/263 |
| 3,968,210 | 7/1976 | Schenkel | 424/235 |
| 3,989,827 | 11/1976 | Apostolatos et al. | 424/235 |
| 4,020,183 | 4/1977 | Asculai et al. | 424/341 |
| 4,100,324 | 7/1978 | Anderson et al. | 428/288 |
| 4,111,844 | 9/1978 | Polony et al. | 252/106 |
| 4,355,021 | 10/1982 | Mahl et al. | 424/28 |
| 4,615,937 | 10/1986 | Bouchette | 428/288 |
| 4,643,939 | 2/1987 | Sugiyama et al. | 428/283 |
| 4,942,029 | 7/1990 | Scheps | 424/78 |
| 5,006,529 | 4/1991 | Resch | 514/721 |
| 5,080,901 | 1/1992 | Hangay et al. | 424/195.1 |
| 5,312,688 | 5/1994 | Honguu et al. | 428/395 |
| 5,403,587 | 4/1995 | McCue et al. | 424/195.1 |
| 5,403,864 | 4/1995 | Bruch et al. | 514/721 |
| 5,416,075 | 5/1995 | Carson et al. | 514/23 |
| 5,531,984 | 7/1996 | Staats | 424/78.07 |
| 5,700,842 | 12/1997 | Cole | 514/721 |

FOREIGN PATENT DOCUMENTS

| | | |
|---|---|---|
| 0 259 249 A3 | 3/1988 | European Pat. Off. . |
| 1 943 694 | 3/1971 | Germany . |
| 25 46 951 A1 | 4/1976 | Germany . |
| 37 23 990 A1 | 2/1988 | Germany . |
| 1408885 | 10/1975 | United Kingdom . |
| 2 211 093 | 6/1989 | United Kingdom . |
| WO 92/18100 A1 | 10/1992 | WIPO . |
| WO93/07250 | 4/1993 | WIPO . |

*Primary Examiner*—Raj Bawa

[57] ABSTRACT

Homogeneous antimicrobial compositions and antimicrobial wet wipes and lotions which include the antimicrobial compositions are described. The homogeneous antimicrobial composition includes at least about 50 weight percent water based on a total weight of the composition and an effective amount of a hydrophobic antimicrobial agent which is uniformly dispersed in the composition. The antimicrobial wet wipe includes from about 150 to about 600 weight percent of the antimicrobial composition based on the dry weight of the wipe. The homogenous antimicrobrial composition may include, based upon the total weight of the composition, (a) from about 0.01 to about 3.0 weight percent of a hydrophobic antimicrobrial agent; (b) from about 1.0 to about 15.0 weight percent of an amide; (c) from about 1.0 to about 30.0 weight percent of a surfactant; and (d) from about 50 to about 98 weight percent water.

32 Claims, No Drawings

ANTIMICROBIAL COMPOSITIONS AND WET WIPES INCLUDING THE SAME

This application is a continuation of application Ser. No. 08/548,347 entitled "ANTIMICROBIAL COMPOSITIONS AND WET WIPES INCLUDING THE SAME" and filed in the U.S. Patent and Trademark Office on Nov. 1, 1995 now abandoned. The entirety of this Application is hereby incorporated by reference.

BACKGROUND OF THE INVENTION

1. Field of the Invention

The present invention relates to an antimicrobial composition and an antimicrobial wet wipe which includes the same. In particular, the present invention relates to an aqueous antimicrobial composition which includes a hydrophobic antimicrobial agent.

2. Description of the Related Art

Conventional antimicrobial compositions have been used in cleansing and cosmetic products such as liquid soaps, shampoos, detergents, lotions, and premoistened wipes. Such compositions have incorporated antibacterial agents to promote the general body hygiene of the user. However, several problems have occurred when attempting to incorporate antibacterial agents into such conventional compositions.

For example, when it is desired that the antibacterial composition be aqueous in nature, the use of antibacterial agents which are hydrophobic, or water-insoluble, has been very limited. The main reason for the limited use of hydrophobic antibacterial agents in aqueous antibacterial compositions is that it has been very difficult to achieve a homogeneous or uniformly dispersed mixture when the hydrophobic antibacterial agents are added to aqueous compositions. Frequently, the hydrophobic antibacterial agents have undesirably precipitated in the aqueous compositions. Such non-homogeneous compositions have also resulted in compositions which have not been completely satisfactory to the consumer due to their cloudy appearance. In an attempt to solve this problem, several conventional compositions have included solvents, such as ethanol and propanol, to achieve solubility of the antibacterial agents. However, conventional compositions which have included such solvents have undesirably resulted in dehydration, stinging and irritation of the skin of the user. The use of such solvents has also undesirably resulted in compositions which are highly unstable, relatively volatile, and difficult to process.

As a result, it has been necessary to use antibacterial agents which readily dissolve in water in many conventional antibacterial compositions. However, such water soluble antibacterial agents have not been completely satisfactory. For example, many of the water soluble antibacterial agents are not as effective as the hydrophobic antibacterial agents.

In an attempt to achieve homogeneous mixtures, many conventional antibacterial compositions have also used large quantities of surface active agents, or surfactants. However, such large quantities of surfactants have lead to excessive foaming of the composition and compositions which are cloudy in appearance. Such excessive foaming and cloudy appearance of the compositions is generally undesirable to the consumer and is particularly undesirable to the consumer when the composition is being used in wet wipes. Typically, consumers of wet wipes desire solutions which do not lather, foam or deposit suds on the skin.

Accordingly, it remains desirable to provide an antimicrobial composition which is stable, highly effective, homogeneous and non-irritating to the skin. In particular, it remains desirable to provide an aqueous antimicrobial solution which includes an effective amount of a hydrophobic antimicrobial agent which is dispersed to provide a homogeneous, clear solution which is non-irritaing to the skin and relatively nonlathering. It is also desirable that such an antimicrobial composition be readily processable. Such an antimicrobial solution is particularly desirable for use with conventional wet wipes and lotions.

SUMMARY OF THE INVENTION

In response to the difficulties and problems discussed above, a new antimicrobial composition which includes a hydrophobic antimicrobial agent and an antimicrobial wet wipe have been discovered.

As used herein, the term amide refers to an organic compound which contains the structural group —CONH$_2$. Suitable amides have the following structural formula:

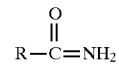

wherein R is a fatty alkyl group.

As used herein, the phrase "antimicrobial" refers to a composition which prevents the growth of *Escherichia coli* (ATCC #11229), *Staphylococcus aureus* (ATCC #6538) (both bacteria), and *Candida albicans* (ATCC #10231) (yeast) in a standard Minimum Inhibitory Concentration (MIC) test. Determining MIC values involves standard microbiological laboratory practices as described in the Examples. In general terms, the MIC value is determined by incubating the test organisms in the presence of various dilutions of the composition and monitoring the growth rate of the test organism. The MIC value is the lowest concentration of the antimicrobial agent which inhibits the growth of the test organism.

As used herein, the term "aqueous" refers to a composition, solution or mixture which contains at least about 50 weight percent water, desirably at least about 70 weight percent water and more desirably at least about 90 weight percent water based on a total weight of the composition, solution or mixture.

As used herein, the term "homogeneous" refers to a composition, solution or mixture whose elements are substantially uniformly dispersed in each other. For example, a homogenous composition may include two or more compounds or elements which are substantially uniformly dispersed within each other. Desirably, the homogenous composition is relatively clear in appearance. In addition, the homogenous composition desirably contains very minimal particulate matter. In one aspect, a homogenous composition is a composition which does not have any particulate matter having a size greater than about 1 micrometer.

As used herein, the term "hydrophobic" refers to a substance which is incapable of completely dissolving in an excess of water. In one aspect, a hydrophobic substance is a substance which does not completely dissolve in an excess of water when allowed to stand for a period of 24 hours.

In one aspect, the present invention concerns a homogeneous antimicrobial composition which comprises, based on a total weight of the composition: (a) from about 0.01 to about 3.0 weight percent of a hydrophobic antimicrobial agent; (b) from about 1.0 to about 15.0 weight percent of an amide; (c) from about 1.0 to about 30.0 weight percent of a surfactant; and (d) from about 50 to about 98 weight percent water. In a particular aspect, the present invention concerns a homogeneous antimicrobial composition which comprises, based on a total weight of the composition: (a) from about 0.01 to about 3.0 weight percent 2,4,4'-trichloro-2'-hydroxydiphenyl ether; (b) from about 1.0 to about 15.0 weight percent of a diethanolamide; (c) less than about 10 weight percent of a nonionic surfactant; and (d) at least about 70 weight percent water.

In another aspect, the present invention concerns a homogeneous antimicrobial composition which comprises an active mixture which includes an effective amount of a hydrophobic antimicrobial agent and an amide, and an aqueous mixture which includes a surfactant and at least about 50 weight percent water based on a total weight of the composition.

In still another aspect, the present invention concerns an antimicrobial wet wipe which comprises an absorbent sheet and from about 150 to about 600 weight percent of a homogeneous antimicrobial composition based on a dry weight of the wet wipe. The composition comprises, based on a total weight of the compositon: (i) an active mixture which includes an effective amount of a hydrophobic antimicrobial agent and an amide; and (ii) an aqueous mixture which includes a surfactant and at least about 50 weight percent water.

In yet another aspect, the present invention concerns a homogeneous antimicrobial composition which consists essentially of, based on a total weight of the compositon: (a) from about 0.01 to about 3.0 weight percent of a hydrophobic antimicrobial agent; (b) from about 1.0 to about 15.0 weight percent of an amide; (c) from about 1.0 to about 30.0 weight percent of a surfactant; and (d) from about 50 to about 98 weight percent water.

Accordingly, the present invention advantageously provides a homogeneous antimicrobial composition which includes a hydrophobic antimicrobial agent and a relatively large percentage of water. The invention further provides antimicrobial compositions which do not require the use of solvents which are volatile and highly flammable.

DETAILED DESCRIPTION OF THE INVENTION

The present invention concerns improved antimicrobial compositions and an antimicrobial wet wipe incorporating such compositions. The different aspects of the present invention will be described for use as antimicrobial compositions for incorporating into conventional wet wipes. However, it is to be understood, that the antimicrobial compositions may be used in the manufacture of other consumer products such as, for example, shampoos, soaps, cleansing agents, detergents, lotions, and the like.

It has been discovered that hydrophobic antimicrobial agents may be used in aqueous compositions to provide homogeneous antimicrobial compositions if the compositions are prepared according to the present invention. The antimicrobial composition of the different aspects of the present invention includes an effective amount of a hydrophobic antimicrobial agent which is at least partially dissolved in an amide and then combined with an aqueous mixture which may include a surfactant.

A wide range of hydrophobic antimicrobial agents which provide antimicrobial compositions may be used in the different aspects of the present invention. The antimicrobial composition may include a single hydrophobic antimicrobial agent or a combination of two or more hydrophobic antimicrobial agents. Desirably, the hydrophobic antimicrobial agent of the present invention is a broad spectrum antimicrobial agent. For example, suitable hydrophobic antimicrobial agents include triclosan, triclocarban, and the like, and combinations thereof. Such hydrophobic antimicrobial agents are generally considered to be water insoluble by those skilled in the art. In a particular aspect, the antimicrobial composition includes triclosan to provide improved antimicrobial effectiveness. As used herein, the term "triclosan" refers to 2,4,4'-trichloro-2'-hydroxydiphenyl ether.

The hydrophobic antimicrobial agent may be present in the composition in any amount which provides an antimicrobial composition. However, if the amount of the hydrophobic antimicrobial agent is too high, the composition may be cloudy and irritating to the skin of the wearer. Moreover, if the amount of the hydrophobic antimicrobial agent is too low, the composition may not be antimicrobial. As set forth above, the antimicrobial effectiveness of the antimicrobial composition can be determined by testing the composition against several known microorganisms. It has been found that antimicrobial compositions of the present invention which include from about 0.01 to about 3.0 weight percent, desirably from about 0.03 to about 1.0 weight percent and more desirably from about 0.05 to about 0.7 weight percent of the hydrophobic antimicrobial agent based on the total weight of the composition are effective against most microorganisms while not irritating the skin. It has also been found that the antimicrobial composition of the different aspects of the present invention is particularly effective when it contains from about 0.01 to about 3.0 weight percent and more desirably from about 0.03 to about 1.0 weight percent triclosan based on the total weight of the composition.

The antimicrobial composition of the different aspects of the present invention may also include other antimicrobial agents which may or may not be considered hydrophobic. For example, the antimicrobial composition may also include p-chloro-m-xylenol, benzalkonium chloride, chlorohexidine gluconate, hexachlorophene, and the like, and combinations thereof.

A wide range of amides which at least partially dissolve the hydrophobic antimicrobial agents may be used in the different aspects of the present invention. For example, suitable amides include alkanolamides, long chain fatty acid diethanolamides, long chain fatty acid monoethanolamides, monoisopropanolamides, and the like, and combinations thereof. In a particular aspect, the amide includes at least about 50 weight percent and desirably at least about 90 weight percent of a lauric diethanolamide based on a total weight of the amide. It has been discovered that the use of a lauric diethanolamide is particularly desirable because of its solubility in water.

The amide may be present in the antimicrobial composition in any amount which provides the desired composition. However, if the amount of the amide is too high, the composition may be cloudy and irritating to the skin of the wearer. Moreover, if the amount of the amide is too low, the hydrophobic antimicrobial agent may not dissolve and the composition may not be homogeneous. It has been found that antimicrobial compositions which include from about 1.0 to about 15.0 weight percent, desirably from about 2.0 to about 10.0 weight percent, and more desirably from about 3.0 to about 5.0 weight percent of the amide based on the total weight of the composition are effective. It has also been found that the antimicrobial composition of the different aspects of the present invention is particularly effective when it contains from about 2.0 to about 10.0 and more desirably from about 3.0 to about 5.0 weight percent of an alkanolamide based on the total weight of the composition.

A wide range of surfactants may also be used in the different aspects of the present invention. It has been hypothesized that the surfactant acts to prevent the precipitation of the active mixture of the hydrophobic antimicrobial agent and amide in the water. Suitable surfactants include those which prevent such precipitation. For example, suitable surfactants may include anionic surfactants, nonionic surfactants, cationic surfactants, amphoteric surfactants and combinations thereof as are well known to those skilled in the art. Suitable anionic surfactants include sodium laureth sulfate, sodium-lauryl methyl taurate, myristoyl sarcosine, sodium dodecylbenzene sulfonate, and the like.

Suitable nonionic surfactants include the polyoxyethylene ethers of the higher fatty alcohols and alkyl phenols; the polyethylene glycols of fatty acids; fatty alkylol amide condensation products; polymers of ethylene and propylene oxides; compounds formed by the addition of propylene oxide to ethylene diamide, followed by the addition of ethylene oxide; fatty acid ethylene oxide condensation products; ethoxylate carboxylic acid; ethoxylate glycerides; and glycol esters. In a particular aspect, the surfactant is desirably a nonionic surfactant, such as octoxynol-9, which provides an improved composition because of it's solubility in water and low level of irritation to the skin.

The surfactant may be present in the antimicrobial composition in any amount which provides the desired composition. However, if the amount of the surfactant is too high, the composition may be cloudy and cause excessive foaming. Moreover, if the amount of the surfactant is too low, the active mixture may precipitate and composition may not be clear and homogeneous. It has been found that the antimicrobial compositions of the present invention which include from about 1.0 to about 30.0 weight percent, desirably from about 1.0 to about 20.0 weight percent and more desirably from about 4.0 to about 10 weight percent of the surfactant based on the total weight of the composition are effective. If it is desired to use the antimicrobial composition in a wet wipe or similar product, the amount of surfactant should not cause excessive foaming of the composition. For example, antimicrobial compositions according to the present invention which include less than about 10.0 weight percent and desirably less than about 7.0 weight percent of the surfactant based on the total weight of the composition have been found to be particularly effective with wet wipes.

The antimicrobial compositions may also include additional elements such as, for example, emollients, perfuming agents, chelating agents, cleansing agents, foam stabilizers, preservatives, protectants, and the like, to enhance the performance of the compositions.

Accordingly, the different aspects of the present invention provide antimicrobial compositions which include hydrophobic antimicrobial agents in an aqueous environment. In a particular aspect, the composition of the present invention defines an MIC value of 100 ppm (parts per million active) or less against $E.\ coli$ (ATCC #11229) and $S.\ aureus$ (ATCC #6538) (both bacteria), and an MIC value of 10,000 ppm or less against $C.\ albicans$ (ATCC #10231) (yeast), desirably defines an MIC value of 10 ppm or less against $E.\ coli$ (ATCC #11229) and $S.\ aureus$ (ATCC #6538) (both bacteria), and an MIC value of 1,000 ppm or less against $C.\ albicans$ (ATCC #10231) (yeast), and more desirably defines an MIC value of 1 ppm or less against $E.\ coli$ (ATCC #11229) and $S.\ aureus$ (ATCC #6538) (both bacteria), and an MIC value of 1,000 ppm or less against $C.\ albicans$ (ATCC #10231) (yeast). Such aqueous, antimicrobial compositions are particularly useful in premoistened wipes and cosmetic products such as liquid soaps, shampoos, and lotions.

The antimicrobial composition may be prepared by a method which involves combining an active mixture of the hydrophobic antimicrobial agent and the amide with a mixture of the surfactant and water. In a particular aspect of the invention, the homogeneous antimicrobial composition includes an effective amount of a hydrophobic antimicrobial agent which is dissolved in an amide to form an active mixture which is then combined with a surfactant/water mixture to provide the antimicrobial composition.

The hydrophobic antimicrobial agent is at least partially dissolved and, desirably, completely dissolved in the amide before the active mixture is combined with the surfactant/water mixture. For example, the active mixture may be mixed for a period of time to ensure the hydrophobic antimicrobial agent is substantially dissolved in the amide. In a particular aspect, the active mixture may be mixed for at least about 10 minutes, desirably at least about 20 minutes, and more desirably at least about 30 minutes to effectively dissolve most of the hydrophobic antimicrobial agent in the amide. Alternatively, the active mixture may be allowed to stand for a sufficient period of time to at least partially dissolve the hydrophobic antimicrobial agent in the amide. The active mixture may also be heated to dissolve at least a portion of the hydrophobic antimicrobial agent in the amide before the active mixture is combined with the surfactant/water mixture. For example, the active mixture may be heated to a temperature of from about 30 to about 50 degrees Centigrade and desirably from about 37 to about 45 degrees Centigrade to effectively dissolve the hydrophobic antimicrobial agent in the amide. In a particular aspect, the hydrophobic antimicrobial agent is dissolved in the amide such that the active mixture does not contain any particulate matter having a size greater than about 1.0 micrometers. Desirably, the active mixture does not contain any particulate matter having a size greater than about 0.50 micrometers and, more desirably, the active mixture does not contain any particulate matter having a size greater than about 0.14 micrometers.

The above described method provides an antimicrobial composition which is homogeneous and relatively clear. After the active mixture has been combined with the surfactant/water mixture, the antimicrobial composition may also be mixed for an effective amount of time to make the composition relatively homogeneous and substantially reduce the size and number of insoluble particulates. For example, the antimicrobial composition may be mixed for at least about 5 minutes and desirably at least about 10 minutes to provide the homogeneous antimicrobial composition.

In another aspect, the present invention concerns an antimicrobial wet wipe which includes the antimicrobial compositions described herein. The antimicrobial wet wipes may appear in several different forms. For example the wet wipes may be in the form of a stack of moistened sheets which have been packaged in a plastic container. The wet wipes may also be in a folded or unfolded configuration. In addition, the wet wipes may be in the form of continuous webs of material which include perforations to separate the individual wet wipes from the continuous web. Such continuous webs may be wound into rolls and also packaged in plastic containers. Such wet wipes can be used for baby wipes, hand wipes, household cleaning wipes, industrial wipes and the like.

Materials suitable for the antimicrobial wet wipe of the present invention are well known to those skilled in the art. The wet wipe can be made from any material suitable for use as a moist wipe, including meltblown, coform, air-laid, bondedcarded web materials, hydroentangled materials and the like and can comprise synthetic or natural fibers or combinations thereof. The wet wipe may have a basis weight of from about 25 to about 120 grams per square meter and desirably from about 40 to about 90 grams per square meter. In a particular aspect, the wet wipe is a coform basesheet of polymeric microfibers and cellulosic fibers having a basis weight of from about 60 to about 80 grams per square meter and desirably about 75 grams per square meter. Such coform basesheets are manufactured generally as described in U.S. Pat. No. 4,100,324 to Anderson et al. which issued Jul. 11, 1978, and which is herein incorporated by reference.

Typically, such coform basesheets comprise a gas-formed matrix of thermoplastic polymeric meltblown microfibers, such as, for example, polypropylene microfibers, and cellulosic fibers, such as, for example, wood pulp fibers. The relative percentages of the polymeric microfibers and cellulosic fibers in the coform basesheet can vary over a wide range depending on the desired characteristics of the wet wipes. For example, the coform basesheet may comprise from about 20 to about 100 weight percent, desirably from about 20 to about 60 weight percent, and more desirably from about 30 to about 40 weight percent of polymeric microfibers based on the dry weight of the coform basesheet being used to provide the wet wipe. Alternatively, the wet wipe 22 can be made from a meltblown sheet of polymeric microfibers having a basis weight of from about 25 to about 120 grams per square meter.

The wet wipes are saturated or otherwise impregnated with the antimicrobial compositions of the present invention, as described herein, by any suitable means such as spraying, dipping, or the like as are well known to those skilled in the art. The amount of the antimicrobial composition which may be added to the wet wipes may vary depending upon the type of material being used to provide the wet wipe, the type of container being used to store the wet wipes, and the desired end use of the wet wipe. Generally, each wet wipe can contain from about 150 to about 600 weight percent and desirably from about 250 to about 450 weight percent of the antimicrobial composition based on the dry weight of the wipe. In a particular aspect wherein the wet wipe is made from a coform material comprising from about 30 to about 40 weight percent polymeric microfibers based on the dry weight of the wipe, the amount of the antimicrobial composition contained within the wet wipe is from about 300 to about 400 weight percent and desirably about 330 weight percent based on the dry weight of the wet wipe. If the amount of liquid is less than the above-identified range, the wet wipe may be too dry and may not adequately perform. If the amount of liquid is greater than the above-identified range, the wet wipe may be oversaturated and soggy and the liquid may pool in the bottom of the container.

Accordingly, the different aspects of the present invention can also advantageously provide an antimicrobial wet wipe which, when compared to conventional wet wipes, has improved antimicrobial effectiveness and is nonirritating to the user. In particular, the different aspects of the present invention can provide an antimicrobial wet wipe which is wetted with an aqueous antimicrobial composition which includes a hydrophobic antimicrobial agent. Such wet wipes can advantageously be used for baby wipes, hand wipes, face wipes, cosmetic wipes, household wipes, industrial wipes and the like.

In yet another aspect, the present invention concerns an antimicrobial lotion which includes the antimicrobial compositions described herein. Generally, the lotion contains from about 10 to about 95 weight percent and desirably from about 50 to about 95 weight percent of the antimicrobial effective composition based on the total weight of the lotion. The lotions of the present invention may also include additional elements such as for example, emollients, oils, emulsifiers, silicones, fatty alcohols, fatty acids, perfuming agents, chelating agents, cleansing agents, foam stabilizers, preservatives, protectants, and the like, to enhance the performance of the lotions. When compared to conventional lotions, the antimicrobial lotion of the present invention has improved antimicrobial effectiveness and is nonirritating to the user. Such lotions can advantageously be used for baby lotions, hand lotions, face lotions and the like.

EXAMPLES

The following examples are presented to provide a more detailed understanding of the invention. The particular materials and parameters are exemplary and are not intended to limit the scope of the invention.

Example 1

An antimicrobial composition according to the present invention was prepared as follows. The composition induded, based on a total weight of the composition, 1.0 weight percent triclosan (2,4,4'-trichloro-2'-hydroxydiphenyl ether), 4.0 weight percent lauric diethanolamide (Lauramide DEA), 8.0 weight percent Octoxynol-9 (CTFA nomenclature) and the remainder water. The triclosan was added to the lauric diethanolamide and the resulting mixture was heated to about 37.7 degrees Centigrade and mixed for about 15 minutes until clear. The water and Octoxynol-9 were blended together. The mixture of triclosan and lauric diethanolamide was then added to the water mixture and mixed for about 10 minutes. The resulting composition was very dear.

The composition was then subjected to the Minimum Inhibitory Concentration (MIC) technique to determine the lowest concentration of the composition which demonstrated a lower growth rate than the growth of the control against *E. coli* (ATCC #11229), *S. aureus* (ATCC #6538) (both bacteria), and *C. albicans* (ATCC #10231) (yeast). The protocol used to determine the MIC values was a standard microdilution method in a 96 well microplate format. Formulations were prepared by serially diluting each sample of the composition in sterile distilled water at dilutions of 0.01, 0.10, 1.0, 10, 100, and 1000 ppm triclosan. The microplate wells were filled with the diluted formulation, a fixed number of microorganisms, and growth media (Mueller Hinton II for *E. coli* and *S. aureus* and Saboraud-Dextrose for *C. albicans*). The inoculums for *E. coli*, *S. aureus*, and *C. albicans* contained $1.3 \times 10^9$ CFU/ml, $4.9 \times 10^8$ CFU/ml, and $1.0 \times 10^7$ CFU/ml, respectively. The microplate was incubated in a THERMOmax™ microplate reader, which was commercially available from Molecular Devices Corporation, a business having offices located in Menlo Park, Calif. under the model numbers 0200-0600 and 0200-0601, for 18 hours at 37 degrees Centigrade. The plate reader was programmed to take optical density readings at 650 nanometers every 30 minutes to monitor the growth rate.

The composition had an MIC value of 1.0 ppm against *E. coli*, 0.1 ppm against *S. aureus* and 1000 ppm against *C. albicans*. The MIC value is the lowest concentration of the composition which demonstrates a slower growth rate than the positive growth control for each microorganism. The control was the same as the compositon tested except that it did not include the triclosan. The control did not exhibit any antimicrobial activity at any dilution tested.

Example 2

An antimicrobial composition according to the present invention was prepared as follows. The composition induded, based on a total weight of the composition, 0.5 weight percent triclosan (2,4,4'-trichloro-2'-hydroxydiphenyl ether), 4.0 weight percent lauric diethanolamide (Lauramide DEA), 5.0 weight percent Octoxynol-9 and the remainder water. The triclosan was added to the lauric diethanolamide and the resulting mixture was heated to about 37.7 degrees Centigrade and mixed for about 15 minutes until dear. The water and Octoxynol-9 were blended together. The mixture of triclosan and lauric diethanolamide was then added to the water mixture and mixed for about 10 minutes. The resulting composition was very clear.

Example 3

An antimicrobial composition according to the present invention was prepared as follows. The composition included, based on a total weight of the composition, 0.5 weight percent triclosan (2,4,4'-trichloro-2'-hydroxydiphenyl ether), 3.0 weight percent lauric diethanolamide (Lauramide DEA), 5.0 weight percent Octoxynol-9 and the remainder water. The triclosan was added to the lauric diethanolamide and the resulting mixture was heated to about 37.7 degrees Centigrade and mixed for about 15 minutes until dear. The water and Octoxynol-9 were blended together. The mixture of triclosan and lauric diethanolamide was then added to the water mixture and mixed for about 10 minutes. The resulting composition was slightly hazy.

Example 4

An antimicrobial composition according to the present invention was prepared as follows. The composition induded, based on a total weight of the composition, 0.5 weight percent triclosan (2,4,4'-trichloro-2'-hydroxydiphenyl ether), 2.0 weight percent lauric diethanolamide (Lauramide DEA), 5.0 weight percent Octoxynol-9 and the remainder water. The triclosan was added to the lauric diethanolamide and the resulting mixture was heated to about 37.7 degrees Centigrade and mixed for about 15 minutes until clear. The water and Octoxynol-9 were blended together. The mixture of triclosan and lauric diethanolamide was then added to the water mixture and mixed for about 10 minutes. The resulting composition was clear.

Example 5

An antimicrobial composition according to the present invention was prepared as follows. The composition induded, based on a total weight of the composition, 0.5 weight percent triclosan (2,4,4'-trichloro-2'-hydroxydiphenyl ether), 3.0 weight percent lauric diethanolamide (Lauramide DEA), 5.0 weight percent Disodium capryloamphodipropionate and the remainder water. The triclosan was added to the lauric diethanolamide and the resulting mixture was heated to about 37.7 degrees Centigrade and mixed for about 15 minutes until dear. The water and Disodium capryloamphodipropionate were blended together. The mixture of triclosan and lauric diethanolamide was then added to the water mixture and mixed for about 10 minutes. The resulting composition was cloudy and an additional 5.0 weight percent Disodium capryloamphodipropionate was added to achieve a clear solution.

Example 6

An antimicrobial composition according to the present invention was prepared as follows. The composition included, based on a total weight of the composition, 0.5 weight percent triclosan (2,4,4'-trichloro-2'-hydroxydiphenyl ether), 1.0 weight percent lauric diethanolamide (Lauramide DEA), 1.0 weight percent rieinol diethanolamide (Rieinoleamide DEA), 5.0 weight percent Octoxynol-9 and the remainder water. The triclosan was added to the lauric diethanolamide and rieinol diethanolamide and the resulting mixture was heated to about 37.7 degrees Centigrade and mixed for about 15 minutes until clear. The water and Octoxynol-9 were blended together. The mixture of triclosan and lauric diethanolamide and rieinol diethanolamide was then added to the water mixture and mixed for about 10 minutes. The resulting composition was very clear.

The examples representatively show that hydrophobic antimicrobial agents can be incorporated into aqueous solutions to provide homogeneous antimicrobial compositions which can be used in conventional wet wipes and cosmetic products such as lotions.

While the invention has been described in detail with respect to specific aspects thereof, it will be appreciated that those skilled in the art, upon attaining an understanding of the foregoing, may readily conceive of alterations to, variations of and equivalents to these aspects. Accordingly, the scope of the present invention should be assessed as that of the appended claims and any equivalents thereto.

I claim:

1. A homogeneous antimicrobial composition which comprises, based on a total weight of said composition:
   a) from about 0.01 to about 3.0 weight percent of a hydrophobic antimicrobial agent which is selected from the group consisting of triclosan and triclocarban;
   b) from about 1.0 to about 15.0 weight percent of an amide which is selected from the group consisting of alkanolamides, long chain fatty acid diethanolamides, long chain fatty acid monoethanolamides, monoisopropanolamides, and combinations thereof;
   c) from about 1.0 to about 30.0 weight percent of a surfactant; and
   d) at least about 70 weight percent water.

2. The antimicrobial composition of claim 1 wherein said antimicrobial agent is water insoluble.

3. The antimicrobial composition of claim 1 wherein said hydrophobic antimicrobial agent is 2,4,4'-trichloro-2'-hydroxydiphenyl ether.

4. The antimicrobial composition of claim 1 wherein said amide is an alkanolamide.

5. The antimicrobial composition of claim 1 wherein said amide is a long chain fatty acid diethanolamide.

6. The antimicrobial composition of claim 1 wherein said amide includes at least about 50 weight percent of a lauric diethanolamide based on a total weight of said amide.

7. The antimicrobial composition of claim 1 wherein said surfactant is a nonionic surfactant.

8. The antimicrobial composition of claim 1 wherein said surfactant is an ethoxylated alkyl phenol.

9. The antimicrobial composition of claim 1 wherein said surfactant is present in said composition in an amount less than about 10 weight percent based on the total weight of said composition.

10. The antimicrobial composition of claim 1 wherein said water is present in said composition in an amount of at least about 90 weight percent based on the total weight of said composition.

11. The antimicrobial composition of claim 1 wherein said composition defines an MIC value of 100 ppm or less against $E.\ coli$, ATCC #11229, and $S.\ aureus$, ATCC #6538, both bacteria, and an MIC value of 10,000 ppm or less against $C.\ albicans$, ATCC #10231, yeast.

12. A homogeneous antimicrobial composition which comprises:
   a) an active mixture which includes an effective amount of a hydrophobic antimicrobial agent which is selected from the group consisting of triclosan and triclocarban and an amide which is selected from the group consisting of alkanolamides, long chain fatty acid diethanolamides, long chain fatty acid monoethanolamides, monoisopropanolamides, and combinations thereof; and
   b) an aqueous mixture which includes a surfactant and at least about 70 weight percent water based on a total weight of said composition.

13. The antimicrobial composition of claim 12 wherein said hydrophobic antimicrobial agent is 2,4,4'-trichloro-2'-hydroxydiphenyl ether.

14. The antimicrobial composition of claim 12 wherein said surfactant is present in said composition in an amount less than about 10 weight percent based on the total weight of said composition.

15. A homogeneous antimicrobial composition which comprises, based on a total weight of said composition:
   a) from about 0.01 to about 3.0 weight percent 2,4,4'-trichloro-2'-hydroxydiphenyl ether;
   b) from about 1.0 to about 15.0 weight percent of a diethanolamide;
   c) less than about 10 weight percent of a nonionic surfactant; and
   d) at least about 70 weight percent water.

16. An antimicrobial wet wipe comprising:
   a) an absorbent sheet; and
   b) from about 150 to about 600 weight percent of a homogeneous antimicrobial composition based on a dry weight of said wet wipe wherein said composition comprises, based on a total weight of said composition:
      i) an active mixture which includes an effective amount of a hydrophobic antimicrobial agent which is selected from the group consisting of triclosan and triclocarban and an amide which is selected from the group consisting of alkanolamides, long chain fatty acid diethanolamides, long chain fatty acid monoethanolamides, monoisopropanolamides, and combinations thereof; and
      ii) an aqueous mixture which includes a surfactant and at least about 70 weight percent water.

17. The antimicrobial wet wipe of claim 16 wherein said absorbent sheet defines a basis weight of from about 25 to about 120 grams per square meter.

18. The antimicrobial wet wipe of claim 16 wherein said hydrophobic antimicrobial agent is 2,4,4'-trichloro-2'-hydroxydiphenyl ether.

19. The antimicrobial wet wipe of claim 16 wherein said hydrophobic antimicrobial agent is present in said composition in an amount from about 0.01 to about 3.0 weight percent based on the total weight of said composition.

20. The antimicrobial wet wipe of claim 16 wherein said amide is a diethanolamide.

21. The antimicrobial wet wipe of claim 16 wherein said amide is present in said composition in an amount from about 1.0 to about 15.0 weight percent based on the total weight of said composition.

22. The antimicrobial wet wipe of claim 16 wherein said surfactant is a nonionic surfactant.

23. The antimicrobial wet wipe of claim 16 wherein said surfactant is present in said composition in an amount less than about 10 weight percent based on the total weight of said composition.

24. The antimicrobial wet wipe of claim 16 wherein said water is present in said composition in an amount of at least about 90 weight percent based on the total weight of said composition.

25. The antimicrobial wet wipe of claim 16 wherein said composition defines an MIC value of 100 ppm or less against *E. coli*, ATCC #11229, and *S. aureus*, ATCC #6538, both bacteria, and an MIC value of 10,000 ppm or less against *C. albicans*, ATCC #10231, yeast.

26. A homogeneous antimicrobial composition consisting essentially of, based on a total weight of said composition:
   a) from about 0.01 to about 3.0 weight percent of a hydrophobic antimicrobial agent which is selected from the group consisting of triclosan and triclocarban;
   b) from about 1.0 to about 15.0 weight percent of an amide which is selected from the group consisting of alkanolamides, long chain fatty acid diethanolamides, long chain fatty acid monoethanolamides, monoisopropanolamides, and combinations thereof;
   c) from about 1.0 to about 30.0 weight percent of a surfactant; and
   d) at least about 70 weight percent water.

27. The antimicrobial composition of claim 26 wherein said composition is clear.

28. The antimicrobial composition of claim 26 wherein said surfactant is present in said composition in an amount less than about 10 weight percent based on the total weight of said composition.

29. The antimicrobial composition of claim 26 wherein said surfactant is present in said composition in an amount of from about 1 to about 20 weight percent based on the total weight of said composition.

30. The antimicrobial composition of claim 1 wherein said composition is clear.

31. The antimicrobial composition of claim 12 wherein said composition is clear.

32. The antimicrobial wet wipe of claim 16 wherein said homogeneous antimicrobial composition is clear.

* * * * *